US012620491B1

(12) United States Patent
Engall et al.

(10) Patent No.: US 12,620,491 B1
(45) Date of Patent: May 5, 2026

(54) INTEGRATED RISK-BASED BLAST AND ENVIRONMENTAL MONITORING WITH MITIGATION SYSTEMS AND METHODS OF PRODUCING SAME

(71) Applicant: Blast Analytics and Mitigation, Inc., Encinitas, CA (US)

(72) Inventors: James Engall, Encinitas, CA (US); Chris Rodewald, Encinitas, CA (US)

(73) Assignee: Blast Analytics and Mitigation, Inc., Encinitas, CA (US)

( * ) Notice: Subject to any disclaimer, the term of this patent is extended or adjusted under 35 U.S.C. 154(b) by 641 days.

(21) Appl. No.: 17/946,999

(22) Filed: Sep. 16, 2022

Related U.S. Application Data

(60) Provisional application No. 63/245,126, filed on Sep. 16, 2021.

(51) Int. Cl.
| | |
|---|---|
| *G16H 50/30* | (2018.01) |
| *G06F 1/16* | (2006.01) |
| *G16H 40/67* | (2018.01) |
| *G16H 50/20* | (2018.01) |

(52) U.S. Cl.
CPC ............. *G16H 50/30* (2018.01); *G06F 1/163* (2013.01); *G16H 40/67* (2018.01); *G16H 50/20* (2018.01)

(58) Field of Classification Search
CPC ........ G16H 50/30; G16H 40/67; G16H 50/20; G06F 1/163
See application file for complete search history.

(56) References Cited

U.S. PATENT DOCUMENTS

| | | | | |
|---|---|---|---|---|
| 2012/0075168 A1* | 3/2012 | Osterhout | ............... | G06F 3/017 345/8 |
| 2016/0187654 A1* | 6/2016 | Border | ............... | G02B 27/0172 359/630 |

* cited by examiner

*Primary Examiner* — Tung S Lau
(74) *Attorney, Agent, or Firm* — Lewis Kohn & Walker LLP; David M. Kohn; Kari Moyer-Henry

(57) ABSTRACT
Methods and devices related to blast and environmental exposure monitoring, introducing a risk-based model for system deployment, and at its highest level, performing head-based blast vectoring within the system for monitoring the exposure and post-event surveillance, including biometric data acquisition, and probing behavioral indicators to perform device driven traumatic brain injury risk assessment.

11 Claims, 16 Drawing Sheets

44

42

70

INTEGRATED RISK-BASED BLAST AND ENVIRONMENTAL MONITORING WITH MITIGATION SYSTEMS AND METHODS OF PRODUCING SAME

FIELD OF THE INVENTION

This application relates generally to the field of environmental hazards from use of weapon systems or explosive devices, such as blast overpressure exposure, for monitoring and mitigation of the effects of weapon system operation or explosive devices to individuals who use them or are positioned around them. Specifically, the methods and devices of the present invention relate to blast and environmental exposure monitoring, introduce a risk-based model for system deployment, and at its highest level, perform head-based blast vectoring within the system for monitoring the exposure and post-event surveillance, including biometric data acquisition, and probing behavioral indicators to perform device driven traumatic brain injury risk assessment.

BACKGROUND OF THE INVENTION

Explosive blasts from high-explosives or propellant explosives have devasting effects on structures, objects, and people in the blast radius. Blast overpressure exposure from these sources has received significant scientific and US congressional attention due to increased awareness of potential adverse outcomes associated with traumatic brain injury (TBI), and more specifically blast-induced traumatic brain injury (bTBI). A specialized novel system that aims to monitor and mitigate blast overpressure exposure is necessary because bTBI. 1) often is the result from exposure to a concussive blast or from repeated exposure to subconcussive blast, 2) presents with symptomology that is dependent on the extent and location of brain injury, and 3) can resolve within days or persist over time (weeks, months, years, or even a lifetime.)

Brain health initiatives and programs that focus on blast exposure monitoring (BEMO) have generated a variety of techniques and leveraged technologies to generate a form of dosimetry to assist users and medical professionals in understanding exposure levels to blast. While rudimentary shot logs, shot counters, and wearable blast sensor technology have been used to approximate and measure dose and cumulative blast overpressure exposure the existing technologies have limitations and a specialized system that can be integrated into standard operating procedures and standard issue equipment to reduce device crowding on a user has yet to be developed to encompass monitoring and mitigation strategies into a single system of the hazards of using weapon systems and/or explosive device exposure.

The current state of the art of blast sensor systems is to detect and record rapid changes in pressure caused by an explosion from a blast event and if worn, to function as a dosimeter by recording characteristic wavefront data from the event to infer concomitant user exposure. Examples of limiting systems in the prior art include those inventions described in U.S. Pat. Nos. 9,339,224, 9,568,389, 9,138,172, 8,984,664, and 8,056,391. One weakness to dosimetry and current blast monitoring techniques is the assumption that the sensor is on the individual/user at the time of the exposure. Additionally, devices that concomitantly monitor exposure and perform post-event monitoring for injury detection have also been developed, as evidenced by U.S. Pat. No. 10,395,501. While these devices provide a method to monitor blast exposure, they lack universal utility for the diverse population of users and the expanding number of possible events from explosions from high-explosives, weapons systems, and explosive devices. Therefore, operator-directed solutions are necessary to advance integrative blast and environmental hazard monitoring, and new concurrent methods to authenticate exposures in real-time and perform injury risk assessments are needed to advance the traditional dosimetry technologies that measure exposure to hazards, such as radiation.

This technology described in the prior art provides less granular exposure related information when variability from a potential blast source is present. Blast sensor systems are used individually or in a plurality to extend the functionality of the system, as further evidenced in US Patent Pub. Nos. 2016/0097756 and US 2011/0191039 and U.S. Pat. Nos. 8,984,664 and 9,568,389.

Inertial sensors, such as accelerometers, have been incorporated into these systems described in the prior art in order to record concomitant movement data to derive force and direction of system movement at the time of a recorded event, as further evidenced in U.S. Pat. Nos. 9,795,177, 10,582,883, 10,667,737, 8,554,509, 5,621,922, and 10,401,380. This method can be used to assess the state of the system, but has limited utility to assess the state and/or disposition of the user. Combining blast sensor and inertial data yields rudimentary blast vectoring capabilities. However, while these systems provide valuable dosimetry information, user variability, such as sensor location, position, and orientation when worn ultimately limit vectoring capabilities of the exposure which can provide inaccurate exposure information, and vectoring between blast sensor systems is dependent on precise time synchronization and networking capabilities, as further evidenced in US Patent Pub. No. US 2016/0097756 and U.S. Pat. Nos. 8,984,664 and 8,111,582.

Acoustic sensors have been used in a similar approach individually or in a plurality to perform shot localization, but the outcome of these embodiments is extrinsic, rather than intrinsic, to the user and do not provide dosimetry related information, as further evidenced in US Patent Pub. No. US 20120082006, International Pat. Pub. No. WO 20120082006 and U.S. Pat. Nos. 6,178,141, 5,976,998, 7,433,266, 7,502,279, 8,063,773, 8,050,141, 8,047,049, 6,965,312, 6,178,141.

There remains a need in the art for systems and devices capable of integrating blast and environmental hazard monitoring, direction finding/vectoring, risk-based assessment, and mitigation strategies within a single, unitary system for real-time operator-directed deployment in order to resolve the known health issues related to TBI and/or bTBI, as further evidenced by U.S. Pat. Nos. 10,338,091, 5,973,998, and 9,289,176. The system of devices presented in this invention disclosure solves the need: 1) risk-based deployment strategies to match the users exposure profile, 2) integrate sensors for exposure monitoring into standard issue equipment to reduce device crowding, 3) to validate user exposure through user and/or device authentication protocols, 4) for supervised blast dosimetry for blast overpressure exposure, including low-level blast and impulse noise, 5) increase the dynamic range capabilities of blast monitoring by incorporating acoustic microphones and pressure sensors into the same system, 6) to link blast overpressure exposure and post-event physiologic and/or behavioral changes indicative of a bTBI, 7) to capture video of the blast event for authentication procedures, 8) to determine angular head-based blast overpressure exposure, 9) provide means to mitigate blast overpressure exposure from weapon systems during training scenarios, and 10) provide training tools as a means to display weapon specific pressure dissipation contours to make the invisible visible.

SUMMARY OF THE INVENTION

The present invention provides and expands upon traditional active and passive blast dosimetry methods by adding user and device authentication within a system for monitoring and mitigating blast and environmental hazards related to the use of weapon systems and explosive devices. The risk-based system is comprised of embodiments to perform passive user-directed and user-authenticated blast and environmental monitoring at its lowest level, active device and device authenticated blast and environmental monitoring, and head-based vectoring of an explosive blast event relative to the individual at its highest level, wherein the system can differentiate exposure to the side of the head of the individual compared to the front or back of the head of the individual. Preferably, the head-based vectoring is in 360-degrees in azimuth, and can be adapted for elevation. Most preferably, the system can accurately measure such varying levels of exposure to the individual in order to provide diagnosis and treatment of bTBI relative to the explosive blast event. The embodiments described below will have the ability to interact with any or all of the technology solutions and or applications outlined for the lower risk and higher risk profiles to achieve comprehensive blast dosimetry, post-event monitoring, notifications, and ultimate integration into the users personal or medical record.

In one aspect, the lowest risk level solution, the methods and systems of the present invention provide a mobile application that updates manual shot logs, passive exposure monitoring and augmented-reality weapon exposure mapping outcomes by leveraging standardized mobile platforms in order to streamline data communications with individuals who have varying risk profiles. In this embodiment, the user interacts with a mobile/portable device and feeds number of shots and corresponding exposure data into their record by querying a database of weapon systems and assigning corresponding exposure profiles to build a cumulative exposure record based upon history of use. In another embodiment, the user selects a weapon system from a pull-down menu to display on device 2D pressure dissipation map around the weapon. In a further embodiment, the user selects a weapon system from a pull-down menu to activate camera, LiDAR, and other capabilities to display an augmented reality 3D pressure dissipation map around the weapon and the user is assigned an exposure profile based upon weapon/device and location of the user in the augmented 2D/3D space.

At a moderate risk-level profile, the present invention provides additional monitoring capabilities to capture blast exposure, post-event biometric monitoring capabilities, behavioral assessment, and user feedback on exposure history and regulatory guidelines. In this embodiment, the monitoring system is a portable device, such as a mobile device, tablet, or laptop, and a wrist wearable device, such as a watch or band, that is equipped with a variety of multimodal sensors to capture blast exposure and changes in both environmental and physiologic state of the user. One feature of this embodiment is that it leverages bioelectric sensors to enable a closed loop circuit that creates a form of "supervised" blast dosimetry, which aim is to directly link exposure to the environmental hazard to the user in real-time. Prior systems "passively" infer blast exposure to the user, which is a major drawback to legacy systems, and this system overcomes this limitation through authentication features. Another feature of the embodiment is that it uses referential historical data within the system to monitor for deviations in the physiologic state of the user in relation to an event. Another feature of this system is coupled acoustic microphone and pressure sensors, which enables a broader dynamic range than systems that use each sensor independently. This feature adds granularity in the exposure data by removing low-pass and high-pass range limitations of each individual sensor type to capture acoustic features of the event. This embodiment will also have the ability to interact with any or all of the technology solutions and or applications outlined for the lower risk or moderate risk configurations.

At the same risk-level profile, the present invention provides additional monitoring capabilities to capture video the blast exposure event to aide in event diagnostics. In this embodiment, an integrated body wearable camera system is equipped with blast and acoustic sensors to trigger a video recording of the event. In a preferred embodiment, the blast overpressure data and video recordings are synchronized and stored in memory locally and transferred to the user's networked profile, personal and/or medical record that can be queried and combined with information from other devices for user and device authentication. This embodiment will also have the ability to interact with any or all of the technology solutions and or applications outlined for the lower risk configurations.

At the highest risk-level profile, the present invention provides system for head-based vectoring of a blast event relative to the user's head, wherein the system can differentiate exposure to the side of the head of the individual compared to the front or back of the head of the individual from a 2-sensor configuration. In a preferred embodiment, the head-based system can be integrated into a head-based accessary, such as a hat, helmet, head band, ear protection, or it can stand alone. In this embodiment, vectoring in 360-degrees in azimuth is performed by comparing data from juxtaposed sensor types. Most preferably, the system can accurately measure such varying levels of exposure to the individual in order to provide more precise head-based exposure data for diagnosis and treatment of bTBI relative to the explosive blast event. This embodiment will also have the ability to interact with any or all of the technology solutions and or applications outlined for the lower risk and moderate risk profiles to achieve similar post event monitoring, "supervised" blast dosimetry, notifications, and ultimate integration into the user's record.

In another aspect, the present invention incorporates mitigation training aides in order to reduce exposures associated with their risk-profile and provide training to an individual with respect to head position and high overpressure zones when operating a weapons system capable of generating a blast exposure to the individual.

In another embodiment, the present invention provides for a blast mitigation training aide for an individual comprising a blast stand, wherein the blast stand reduces reflective blast exposure from a ground location by elevating the individual's shooting position. Optionally, the system is coupled to a blast filter, wherein the blast filter attenuates reflective blast exposure to the users.

In yet another embodiment, the present invention provides for a specialized blast monitoring and mitigation system, wherein the system is utilized to inform users of exposure profiles associated with weapons/device-based exposure.

In another aspect, the present invention provides a system for monitoring and mitigating exposure to environmental hazards to a user from weapons or devices, comprised of a digital application on a portable mobile device; providing at least one wearable component for the user to wear; providing a plurality of sensors, wherein the plurality of sensors is connected to the at least one wearable component for the user to wear and wherein the at least one wearable component can detect, monitor and record exposure to the environmental hazards; and providing post-event monitoring for detection of changes in behavioral, physiological, and cognitive markers of head trauma, body trauma and environmental hazard exposure. Preferably, the exposure to the environmental hazards is at least one of blast overpressure, acoustics, microwaves, radiation and chemicals, and which further results in at least one selected from the group consisting of head trauma, body trauma and environmental hazard exposure. Optionally, the system further provides a risk-based profile for the user related to the user's operation of a weapons system or explosive device. Most preferably, the detection, monitoring and recording of the environmental hazards results in supervised, real-time authentication capabilities.

In yet another aspect, the plurality of sensors comprises unimodal or multimodal sensors further connected to at least one selected from the group consisting of a computer, microprocessor, controller unit and memory. Optionally, the memory is one selected from the group consisting of flash, solid state and cloud-based storage. Preferably, the system further comprises a head-mounted system for the user to wear; a set of at least two juxtaposed sensors; and a means to calculate a vector of the exposure in relation to the user's head position.

In another aspect, the present invention provides for a wearable device for a user providing a varying risk level of exposure to weapon systems or biological or chemical agents, comprising: a component for application to a body section of the user, wherein the component initiates at least one protocol to assess biological, physiological, or behavioral indicators of an injury; and a wired or wireless communication element connecting the component to a computer or portable mobile device.

Alternatively, the present invention provides for a stand or platform for a user of a weapon system to increase the distance between the weapon system and a reflective surface, wherein the stand or platform can be equipped with at least one material that reduces exposure levels from the reflective surface to the user. Specifically, the reflective surface is a firm area comprising ground or a floor.

BRIEF DESCRIPTION OF THE DRAWINGS

The novel features of the present invention are set forth herein embodied in the form of the claims of the invention. Features and advantages of the present invention may be best understood by reference to the following detailed description of the invention, setting forth illustrative embodiments and preferred features of the invention, as well as the accompanying drawings, of which:

DETAILED DESCRIPTION OF THE INVENTION

Described herein are methods, devices and systems specifically configured to aid in the monitoring and mitigation of the detrimental effect of blast exposure to individuals. The integrated blast monitoring and mitigation system is a compilation of products that are used for blast monitoring and mitigation. Each product may function independently or in tandem with other products that monitor and/or mitigate blast exposure to help understand and potentially decrease risk associated with blast exposure in both training and real-world environments.

Figure 1:
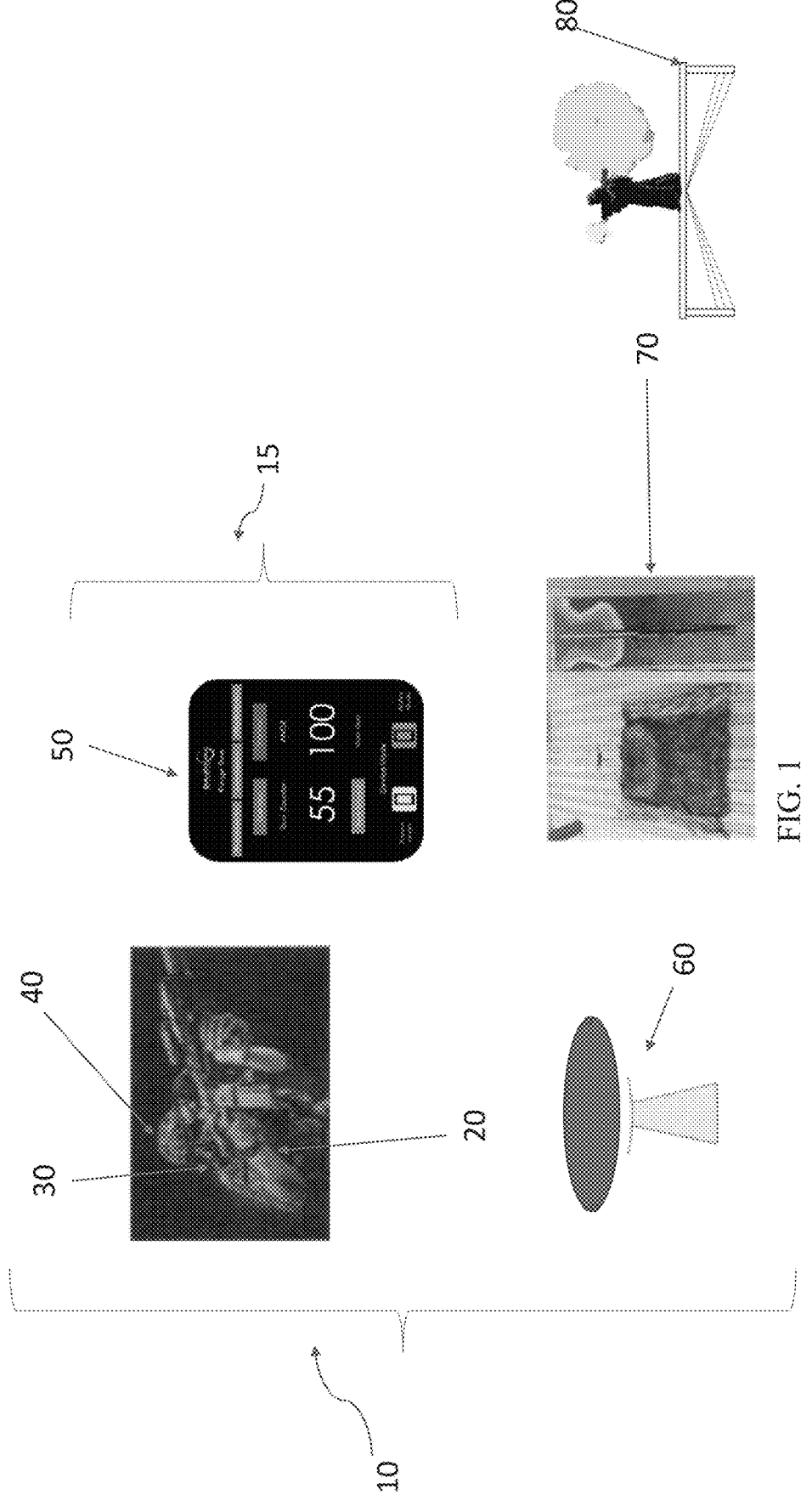
FIG. 1 shows components of the system of the present invention enabling user-authenticated, and unsupervised or supervised device-authenticated environmental hazard monitoring.
Figure 2:
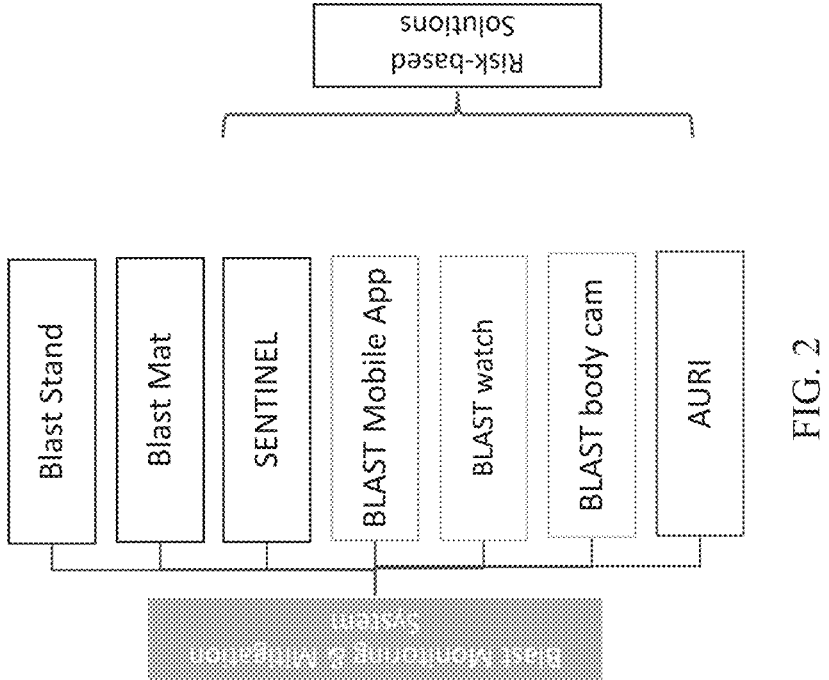
FIG. 2 shows the flow chart schematic of the risk-based blast monitoring and mitigation system of the present invention.

As summarized at FIGS. 1 & 2, the present invention provides for a specialized risk-based blast monitoring and mitigation system that can be used to inform people of interest, such as users and medical professionals, of the exposure profiles associated with blast exposures. FIG. 1 describes the array of components of the preferred embodiments of the present invention. System 10 enables user-authenticated, unsupervised or supervised device-authenticated environmental hazard monitoring. This approach leverages a novel risk-based model 15 and deploys a series of wearable devices based on the user's exposure profile, including watch 20, body camera 30 and head accessory 40. Optionally, the system comprises application based mobile device 50. The approach also leverages mitigation strategies to decrease exposure from possible hazards, including blast station 60, blast mat 70 and/or blast stand 80. This system includes a blast monitoring system, digital application, wearable wrist smart device, blast body cam system, and head-based accessories to perform head-based vectoring in 360-degress in azimuth. Accurately measuring user exposure, post-event monitoring, and the head-based vector of the explosive blast event is a critically important step to assist users and medical professionals in the diagnosis and treatment of bTBI. FIG. 2 shows a flow chart schematic of system 10. This novel approach to environmental hazard monitoring, such as blast overpressure and acoustic exposure, is calculated by user provided information on type of potential exposures, frequency of exposure, and potential future exposure based upon profession.

Understanding the type and direction of exposure to the head is critically important to all forms of TBI, especially bTBI. Since blast exposures to the side, front, and back of the head may yield different outcomes, and head movement may change the exposure direction and intensity, a head-based monitoring system that provides accurate head-based exposure data is critically important. The configuration of the system described herein also accounts for the unique stature and physical characteristics of each user, providing even greater granularity which is necessary information for users and medical professionals in analyzing, diagnosing and treating bTBI.

The system of the present invention is designed to specifically address shortcomings in the current state of the art. In addition to head-based vectoring by recording from two or more directly-linked blast sensors, valuable information that can be used in signal processing algorithms for event validation, artifact filtering, and event classification from this system design.

The improvements over the prior art and advantages of the preferred embodiments of the present invention include:

1) Rudimentary blast exposure monitoring without dosimetry can be achieved through simple shot counting. Shot counters can be manual or digital devices. Examples of limiting systems in the prior art include those inventions described in U.S. Pat. Nos. 10,401,380 and 8,826,575, and US Pat. Pub. No. US 20150347079.

Our mobile/portable device system makes significant improvements on shot counting systems through user and device authentication protocols, and hardware upgrades by leveraging hardware typically found in portable mobile devices. This enables users to perform shot counting and dosimetry in one system. Passive shot counting and dosimetry is achieved through user input into a program or application and device protocols. Passive shot counting and dosimetry is achieved by the user selecting a weapon system or explosive device from a weapon exposure library and exposure data is assigned based upon user input on the number of shots fired or types of exposures. Active shot counting and dosimetry is achieved through device protocols, device acoustic microphone and inertial sensor hardware activation. The user selects a weapon system or explosive device from a weapon exposure library, the device's selected hardware is then used to trigger event related data, and exposure data is assigned based upon user input before the exposure. Authenticated shot counting and dosimetry is achieved through device protocols, device acoustic microphone, inertial sensor hardware activation, and/or communicating with body worn sensor systems in a wired or wireless configuration. The user selects a weapon system or explosive device from a weapon exposure library, the device's selected hardware is then used to trigger event related data, exposure data is assigned based upon user input before the exposure, and the user provides additional input to confirm the exposure data. In the preferred embodiment this system can also be enabled to interact with technologies such as the smart watch, body camera system, head-based devices, or smart blast station embodiments of the present invention to obtain environmental data or it can utilize other range or field related equipment input that may be available to provide enhanced environmental input.

2) Current blast monitoring systems are designed to detect and record rapid changes in pressure caused by an explosion from a blast event and if worn, to function as a blast dosimeter by recording characteristic wavefront data from the event to infer concomitant user exposure. Prior devices provide these blast monitoring capabilities, as evidenced by U.S. Pat. Nos. 9,339,224, 9,568,389, 9,138,172, and 8,984,664.

The systems and devices of the present invention make significant improvements on these devices through user and device authentication protocols, and new hardware upgrades, such as integrating acoustic microphones and pressure sensors into the same system to increase the dynamic range capabilities of the system. This enables a broader dynamic range than systems that use each sensor independently. This feature adds granularity in the exposure data by removing low-pass and high-pass range limitations of each individual sensor type and can be configured with power consumption management protocols to conserve battery life. Bioelectric sensors can be used to create open or closed circuits, and new procedural routines across integrated hardware can solve this problem by linking the user to the exposure event.

3) In addition, current blast monitoring wearable devices may or may not be worn by the user at the time of the exposure events. Prior devices provide indirect or "unsupervised" environmental blast monitoring capabilities, as evidenced by U.S. Pat. Nos. 9,339,224, 9,568,389, 9,138,172, and 8,984,664.

Our system makes significant improvements on these devices by incorporating supervised device authenticated environmental blast monitoring capabilities. Our wrist and head-based wearables incorporate bioelectric sensors to create open or closed circuits, and new procedural routines across integrated hardware solve this problem by directly linking the user to the exposure event.

4) Current blast monitoring wearable devices are configured to only detect blast exposure events, and not perform post-event physiologic and behavioral monitoring. Prior devices provide these blast monitoring capabilities, as evidenced by U.S. Pat. Nos. 9,339,224, 9,568,389, 9,138,172, and 8,984,664. Prior devices provide post-event monitoring capabilities that are not linked to blast exposure events, are evidenced by U.S. Pat. Nos. 10,667,737, 10,401,380, and 10,292,650.

Our system makes significant improvements on these devices by adding specificity of the systems by linking changes in physiology and behavior to a blast overpressure exposure event. This added granularity assists users and medical professionals in the diagnosis and treatment of bTBI.

5) Current blast monitoring systems and methods provide rudimentary vectoring capabilities. In one embodiment, vectoring is achieved through a plurality of independent wirelessly networked blast sensor systems, as evidenced by U.S. Pat. Nos. 9,339,224, 9,568,389, 9,138,172 and 8,984,664. These systems frequently rely on knowing the exact location of the sensor systems, inertial sensors, and precise time synchronization between systems. If the system position is unknown, or if the systems timing become desynchronized, vectoring and spatial reconstruction abilities become invalid and limited rudimentary spatial reconstruction may be inaccurate. In another system, a plurality of interconnected sensors is incorporated into a helmet to perform vectoring, as evidenced by U.S. Pat. No. 8,984,664. In yet another system, a plurality of sensors are embedded into a collar that is worn around the neck perform vectoring of the blast, as evidenced by U.S. Pat. No. 8,111,582.

Our system significantly improves these systems by performing within system head-based vectoring capabilities by having two directly linked blast sensors within the same system, in which prior systems relied on more than two sensors. Networked blast sensor systems require input from other blast sensor systems to perform vectoring and/or spatial mapping of blast events. Vectoring and spatial mapping are dependent upon precise time synchronization, spectral and intensity differences between these blast sensor systems. Interconnected blast sensor systems that are wired together currently offer the most precise time synchronized recordings between systems, whereas wireless systems may suffer from clock drift that yields desynchronized time clocks between systems and therefore inaccurate information may be used to solve the vectoring of the exposure. Our system is currently designed to be configured as a wired system. Future wireless master/slave I/O configurations will also be compatible with our system. Vectoring errors are generated with a 2-sensor solution to perform vectoring of the blast wave origin solely on short duration recordings that rely on intersensory-timing differences. Our system solves these vectoring errors by also leveraging intensity and spectral differences collected at each sensor. To induce spectral differences, we have a specialized screen/filter to induce spectral changes in the recorded data to calculate whether the blast origin is in front or the back of the system. Additionally, since the head is not stationary, our head-based system accounts for these additional degrees of movement and overcomes problems of prior systems that are in a fixed position on the body or neck. This capability enables fine and coarse angular head-based vectoring capabilities, which has differential loading characteristics on risk-based models of bTBI. While our system is designed with accelerometers, their primary function is to collect movement and force data. Validation of recorded data from a single blast sensor configuration requires extensive on board and offline analytics. Our system was designed to perform cross-sensor validation to minimize on board/offline analytics, reduce data collection related errors, and decrease power consumption.

6) Current head devices, such as U.S. Pat. No. 8,984,664 the helmet blastometer, uses a plurality of built-in sensors to capture time of arrival and event waveform data across the plurality of sensors to calculate the vector of the blast event. This integrated helmet has extensive hardware and is post-processing intensive to perform vectoring, whereas our system's two sensor and specialized filter design reduces the necessary hardware and post-processing steps to achieve the vectoring outcome which is a significant advantage. The helmet blastometer is an integrated blast sensor helmet. This unified system limits users to this specific product.

Our system is designed to be integrated into or as an accessary to multiple types of head gear, such as helmets, hats, headbands, hearing protection, eye protection, or any other head-based accessories.

7) Current blast mitigation systems have limited form and function during weapon system training scenarios that expose users to blast. Examples of limiting systems in the prior art include those inventions described in U.S. Pat. No. 7,017,705.

Our system significantly improves these systems by several approaches. For known weapon systems that produce blast overpressure exposure, reducing the initial blast wave front through filtering, and increasing the distance of reflective surfaces, such as the ground can have profound effects in reducing blast overpressure exposure. Prior systems that have similar features to elevate users are evidenced by U.S. Pat. No. 10,849,321. While these systems are designed to elevate users, their construction may not withstand the forces of blast overpressure and are not compatible with filtering materials to attenuate blast overpressure. Additionally, displaying weapon specific pressure dissipation contours in 2D or 3D representations or maps can alter behavior in subtle ways and are tools that can also be used to reduce blast overpressure exposure.

The current state of the art of shot counters/logs come in manual, analog and digital systems. Examples of limiting systems in the prior art include those inventions described in U.S. Pat. Nos. 10,401,380 and 8,826,575. Manual methods require the user to log the weapon and number of shots fired during and or following operation. Analog methods require the user to interact with a device to count the number of shots fired, and then the user logs the results following operation. Digital methods require the use of accelerometers or magnets to count the number of rounds fired. The problem with these methods is that they lack dosimetry information that can be transferred to the user and or the user's personal or medical record to understand their exposure level, they often lack accuracy and there is an increased potential for user error.

Figure 3:
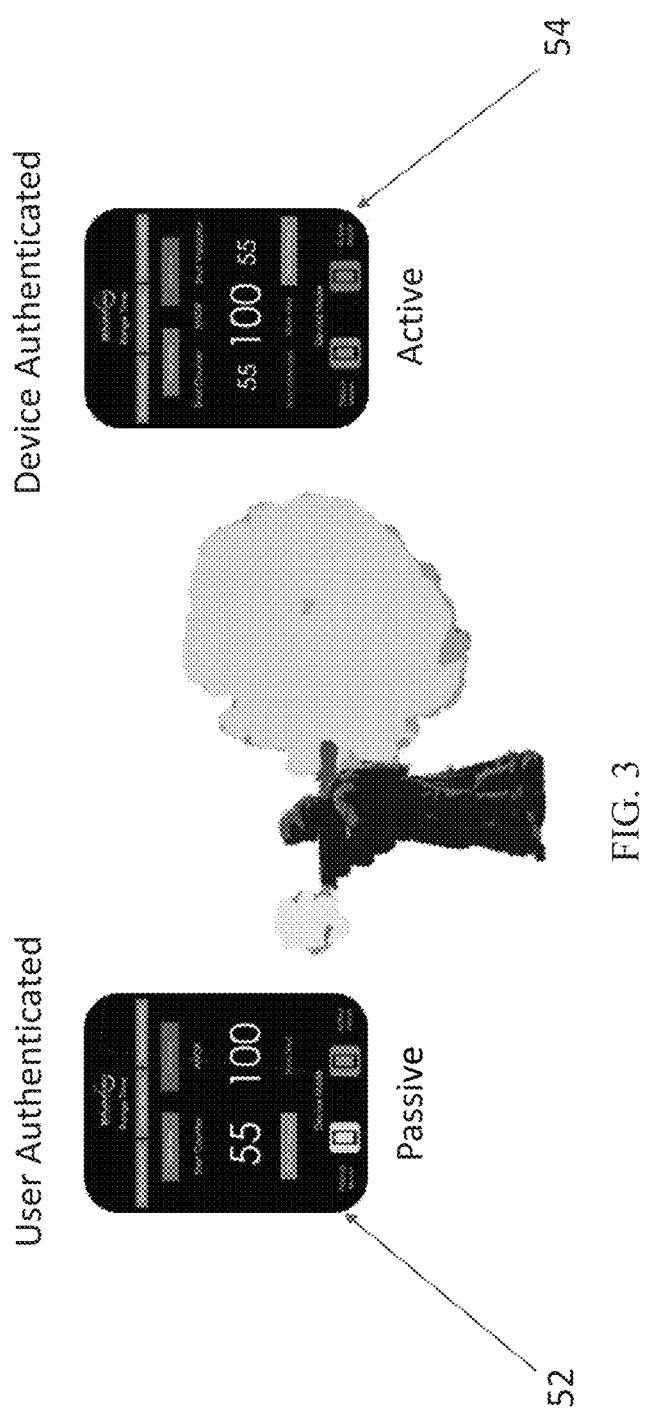
FIG. 3 shows application driven passive user-authenticated and active device-authenticated environmental hazard dosimetry for low-risk users.

The application/mobile application of the present invention performs shot counting and logging through a user interface and standard mobile platform sensors, thereby solving the limitations described above by adding a layer of information to the user's connected account by querying a proprietary weapons library to pull exposure data, as shown at FIG. 3. Passive user-authenticated 52 dosimetry is a method to capture exposure history by using a weapon specific shot log and then querying a weapon specific pressure database and applying incident pressure exposure values are logged into the user's records on the device, and can be pushed to external database. Active device-authenticated 54 dosimetry is a method to capture exposure history by utilizing built in on device sensors, such as the acoustic microphone and inertial sensors. The user selects the weapon system before initializing the trigger mode to perform shot counting, and corresponding weapon specific weapon specific pressure database is queried and corresponding incident pressure exposure values are logged into the user's record on the device, and can be pushed to external database.

This weapons signature library contains pressure recordings from the approximate location of the user's body. Passive user-authenticated 52 and unsupervised active device-authenticated 54 dosimetry exposure data is then transferred to the user's account upon closing the session and confirming basic weapon usage information. Additional features of the mobile application can include weapon specific blast overpressure 2D spatial maps and exposure prediction data that is derived by LiDAR or other spatial technology build-in to some mobile devices. In another embodiment, the user can manually input or confirm type of weapon used, shooting position, number of shots fired, type of shooting facility to generate a form of passive user-authenticated dosimetry 52. In another embodiment this system can also be enabled to interact with technologies such as the smart blast station embodiment of the present invention, the blast watch, the blast cam, or head-mounted system AURI system to obtain environmental data, or it can utilize other range or field related equipment input that may be available to provide enhanced environmental input.

In a preferred embodiment of the present invention, the mobile application upgrades manual shot logs and shot counters that are linked to the application user and provides dosimetry and weapon specific pressure contour maps. This is accomplished by a user opening the application, signing into their account, and establishing a recording. The user pulldown menus have manual and automatic entry capabilities making it easier for the user and increasing accuracy. Shot counting is achieved manually (passive user-authenticated) and/or by using the mobile device's microphone or inertial sensors to capture high-amplitude acoustic movement signals to trigger an event recording (i.e., active device authenticated dosimetry). Traditional sensor-based exposure monitoring provides trigger-related feedback about the blast exposure. Passive user-authenticated exposure monitoring is achieved through manual input into the program/application, or alternatively activating and starting the mobile application to trigger a recording on an upcoming exposure event by pulling standardized weapon exposure data from specific weapons in the weapons library, and then attributing that exposure data to the user. Additional information can be collected, such as confirmation of direct exposure and indirect exposure is achieved at the end of the session by the user exiting the recording, and the program prompting user data (i.e., type of weapon used, shooting position, number of shots fired, type of shooting facility, etc.).

Figure 4:
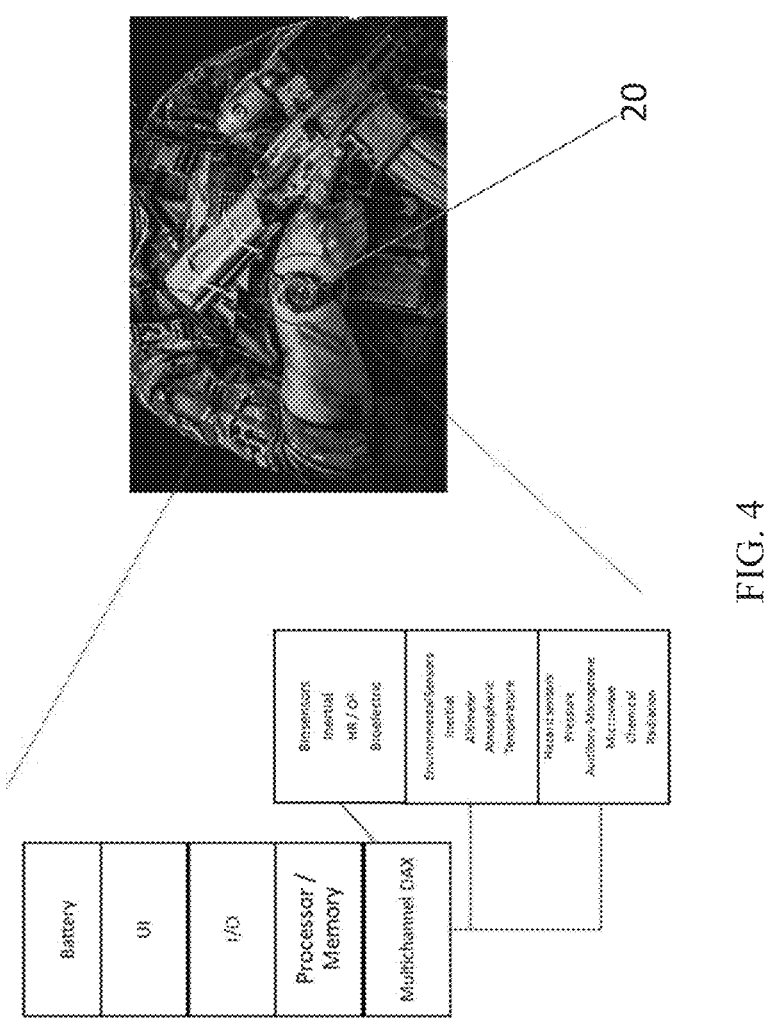
FIG. 4 shows a preferred embodiment of the smart watch system of the present invention, including a schematic of a closed biometric circuit with integrated plurality of unimodal and/or multimodal sensors.

In an alternative embodiment, the present invention further provides for watch 20 comprising a closed biometric circuit with integrated multimodal sensors to perform dosimetry and user validation in real-time (FIG. 4). FIG. 4 shows a preferred embodiment of watch 20, including a schematic of a closed biometric circuit with integrated plurality of unimodal and/or multimodal sensors. Supervised device-authenticated dosimetry is achieved through this hardware configuration and software routine to directly link an exposure event to the user. This embodiment of watch 20 can include additional hazard sensors and standard biometric sensors to perform post-event monitoring. In this embodiment, watch 20 of the present invention can be equipped with various microphones to detect infrasound or ultrasound, and microwave sensors to monitor for hypersonic weapon exposure. In a preferred embodiment, the system is equipped with acoustic and pressure sensors with overlapping sensitivities to increase the dynamic range of the system to detect blast exposure. In another embodiment this system can be equipped with microwave sensors to detect microwave exposure. This embodiment can also be equipped with lateral flow biosensors to increase the detection of bTBI. Prior TBI systems lack blast detection and focus on specific behavioral constructs that are indicative of a TBI, as evidenced in the prior art by U.S. Pat. No. 10,667,737.

Figure 5:
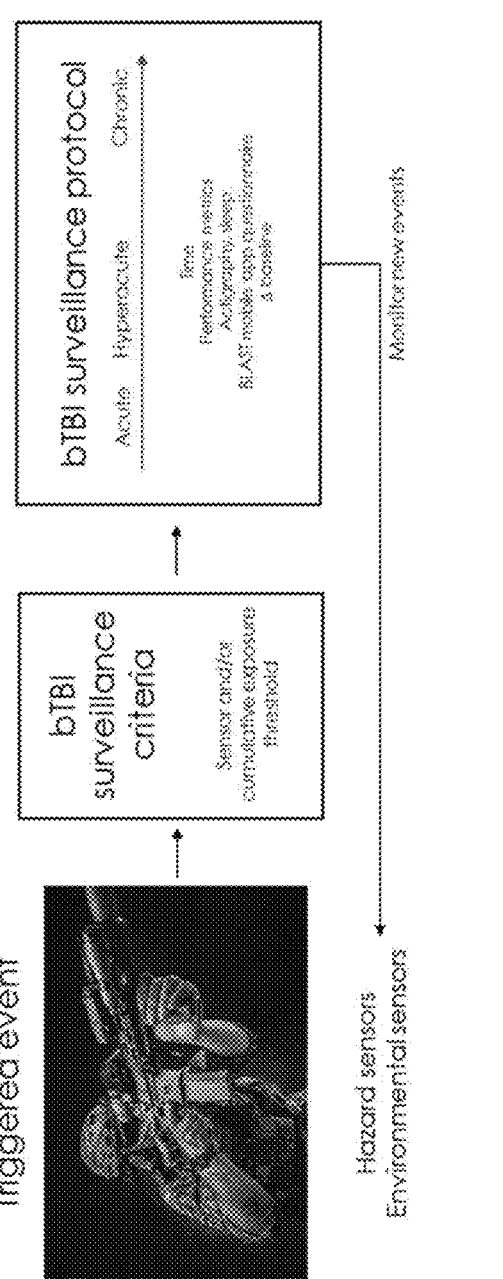
FIG. 5 shows a flow diagram of post-event monitoring of a user for bTBI surveillance.

Additionally, the watch 20 of the present invention further comprises performing post-event monitoring of the individual user for bTBI surveillance (FIG. 5). Following a supervised device-authenticated triggered event, routines that activate on device sensors to monitor and detect physiological and behavioral markers can be initiated to warn the user of exposure related changes indicative of an ailment, such as bTBI. The preferred embodiment of this feature utilizes multimodal sensors that track a variety of behavioral anchors that may be indicative of a TBI.

Figure 6:
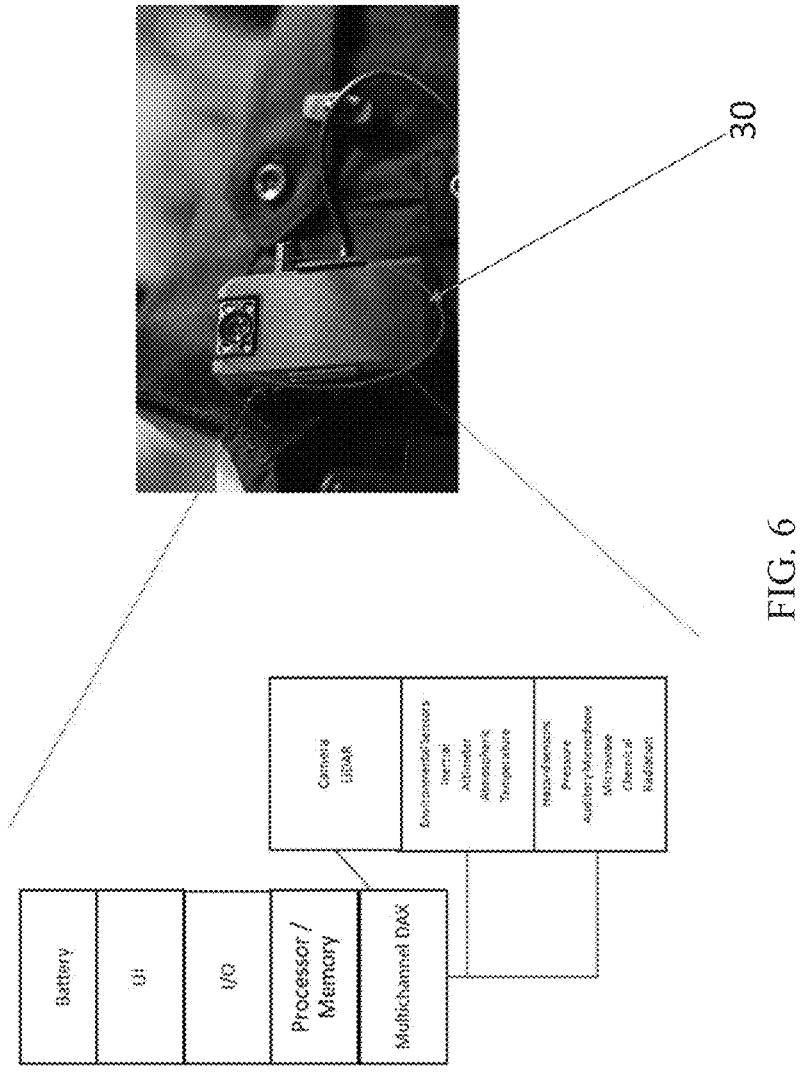
FIG. 6 shows a preferred embodiment of the body camera system of the present invention, including a schematic with integrated plurality of unimodal and/or multimodal sensors.
Figure 7:
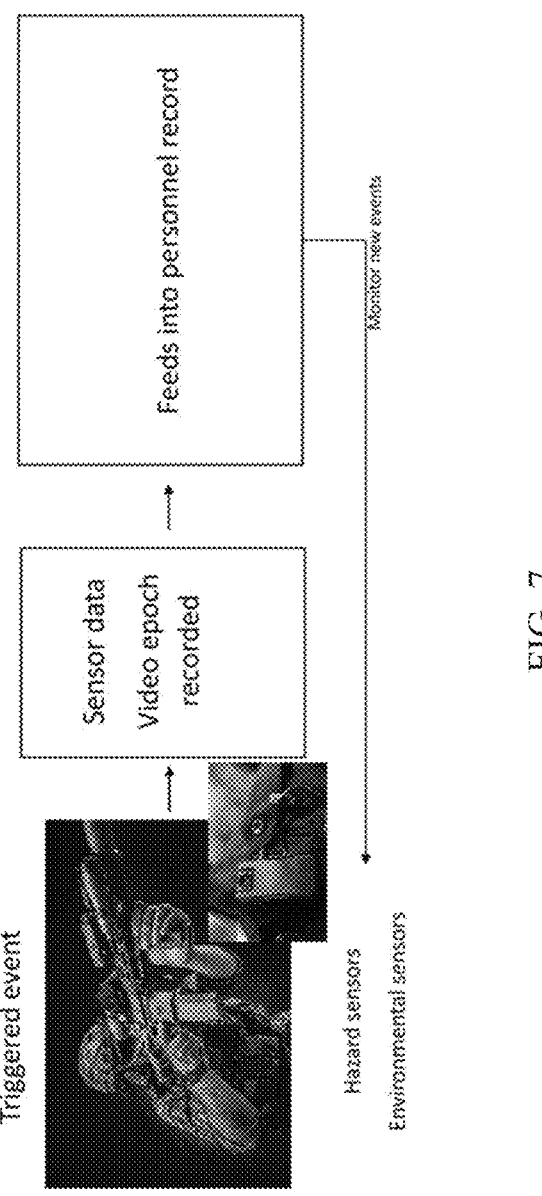
FIG. 7 shows a flow diagram of a triggered event and recorded video being fed into a user's personnel record.

Alternatively, this system may be integrated into body camera 30 or other similar system which can capture a video of a blast event (FIGS. 6 & 7). FIG. 6 shows a preferred embodiment of body camera 30, including a schematic with integrated plurality of unimodal and/or multimodal sensors. Unsupervised device-authenticated dosimetry is achieved through hardware configuration and software routines to record and link an exposure event to a potential user.

FIG. 7 shows a flow diagram of a triggered event and recorded video being fed into a user's personnel record. Following an unsupervised device-authenticated triggered event, routines that activate on device sensors to acquire a video record to link a potential user of exposure to an exposure event.

Figure 8:
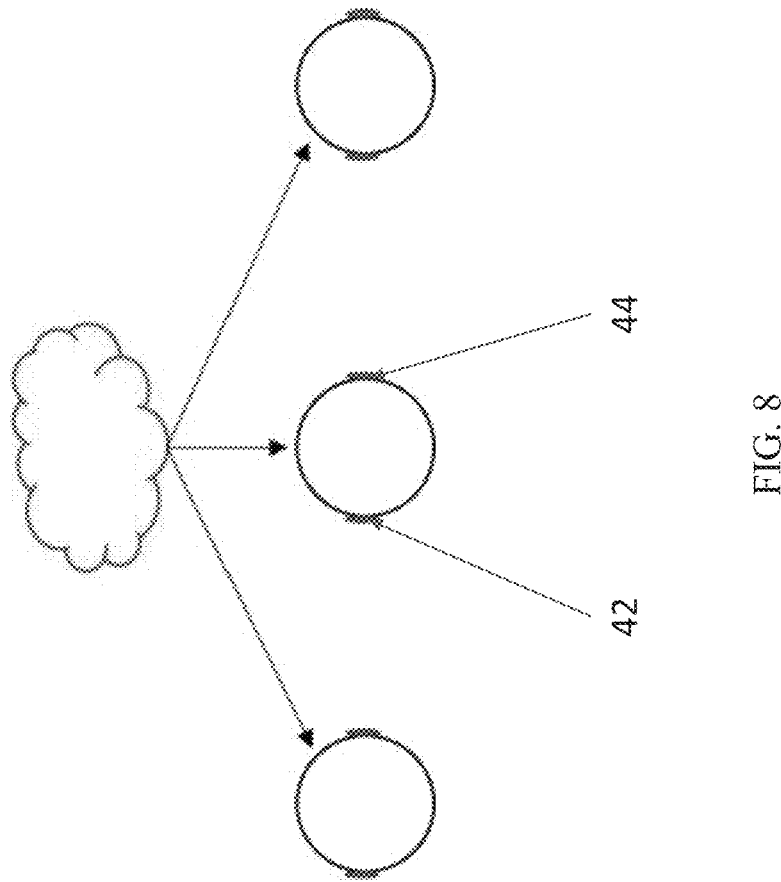
FIG. 8 shows how the devices of the present invention are designed to be analogous to the ears of humans through use of blast pressure sensors.

The head-mounted system is designed to function in an analogous way to the ears of humans, except to detect blast overpressure. FIG. 8 shows how the devices of the present invention are designed to be analogous to the ears of humans, and in the preferred embodiment uses two juxtaposed interconnected blast pressure sensors 42, 44 to derive intersensor-timing differences, intersensor-intensity differences, and intersensor-spectral differences to perform head-based blast localization/vectoring.

Figure 9:
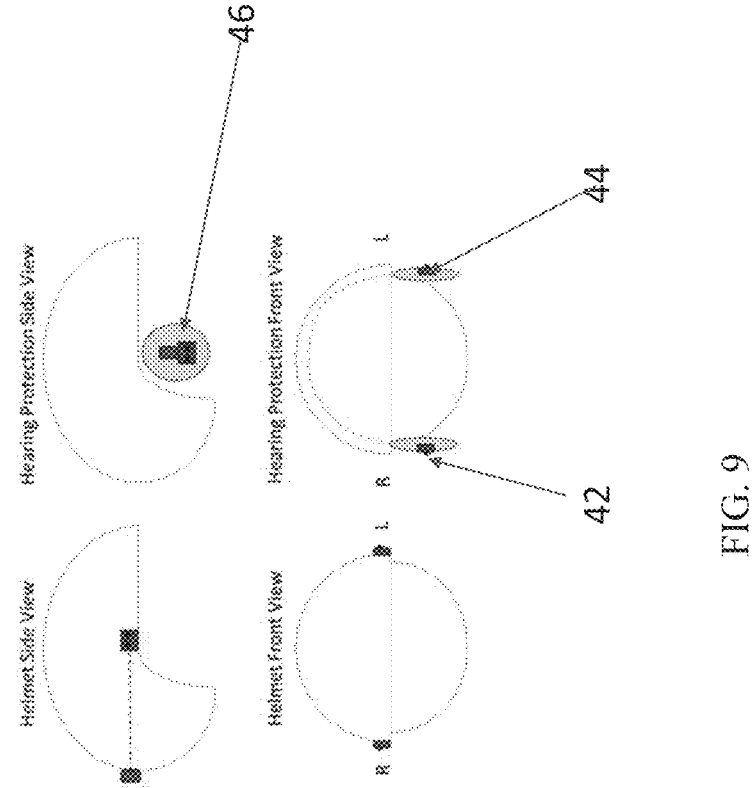
FIG. 9 shows various examples of the configurations of the devices of the present invention as applied in relation to helmets, ear protection and/or other head accessories.

FIG. 9 shows various examples of the configurations of the devices of the present invention as applied in relation to helmets, ear protection and/or other head accessories. The configuration of the devices can be mounted to or integrated into these head-based accessories.

Figure 10:
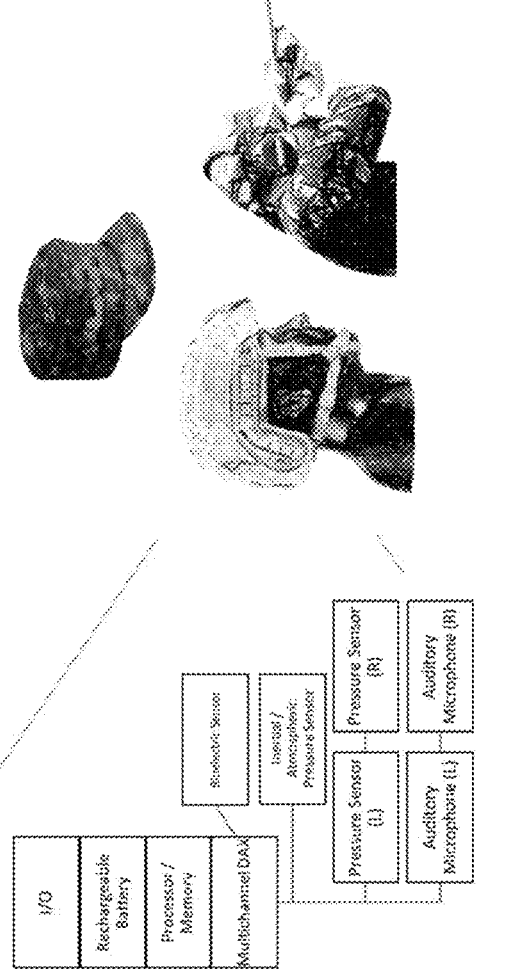
FIG. 10 shows a preferred wiring diagram of the main housing and connected sensors described in the present invention.

As shown at FIG. 9, two juxtaposed interconnected blast pressure sensors 42, 44 are placed at standardized locations on the sides of the head, either connected directly to helmet 40 or contained within ear protection 46 to collect blast dosimetry. Fine (as low as 1-degree coordinates) and coarse (90-degree coordinates) spatial vectoring of the blast wavefront is then achieved through specific hardware configurations (FIG. 10) and proprietary vectoring algorithms of the present invention. The approximate configuration of the blast sensors produces lead and lag times when the blast wavefront arrives and triggers a recording at each sensor. In the preferred embodiment, two juxtaposed interconnected blast pressure sensors 42, 44 are coupled to acoustic microphones to increase the dynamic range of the triggered exposure recording to facilitate blast vectoring from a short duration exposure recording. The resolution of the vectoring capability is related to the sampling rate of the data acquisition system with coarse quadrant localization capability from lower sampling rate systems and fine degree/multi-degree resolution from higher sampling rate systems.

Figure 11:
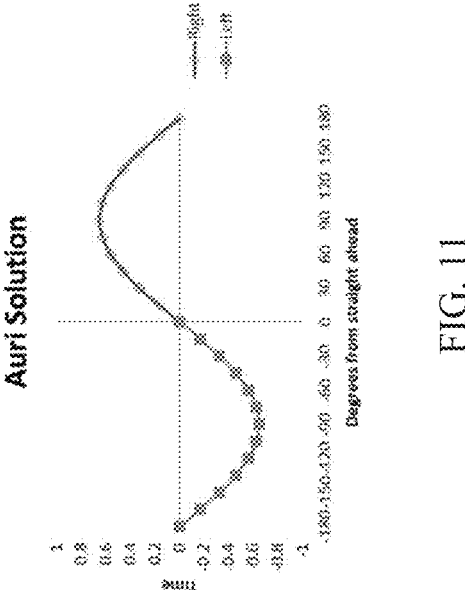
FIG. 11 shows a sample of a head-based intersensor vectoring algorithm outcome in 360 degrees in azimuth from the system of the present invention.

The intersensor-time difference lead and lag times are then used to calculate whether the direction of the blast wavefront is to the right or the left of the user, as represented at FIG. 11. Left and right sides of the head are represented with negative and positive values, respectively. Left and right sided exposures are confirmed from intersensory-intensity differences as the leading sensor may record higher intensities and the lagging sensor may record lower intensities due to shadowing.

Figure 12:
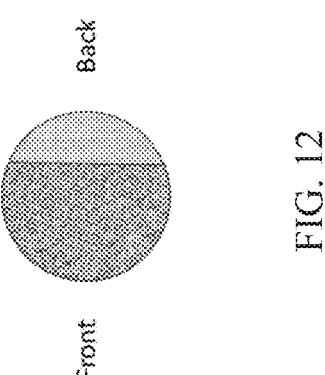
FIG. 12 show an example of a specialized filter screen to produce changes in spectral content as measured by systems described herein to enhance front and back vectoring capabilities of the system.

Intersensor-intensity differences are also used to calculate direction of the blast wavefront. Front/back calculation confusion errors occur when the wavefront arrives at both sensors simultaneously. This is resolved by specialized filter screens (FIG. 12) or other features that induce spectral disparities in the recordings, depending on whether the origin is in front or behind the user. Additional sensors can be added to the configuration to add pitch/yaw, or to solve the vector of the blast wavefront without the filter screens. In another embodiment, the HEAD-MOUNTED SYSTEM (AURI) is comprised of a closed biometric circuit for user-authenticated dosimetry.

Figure 13:
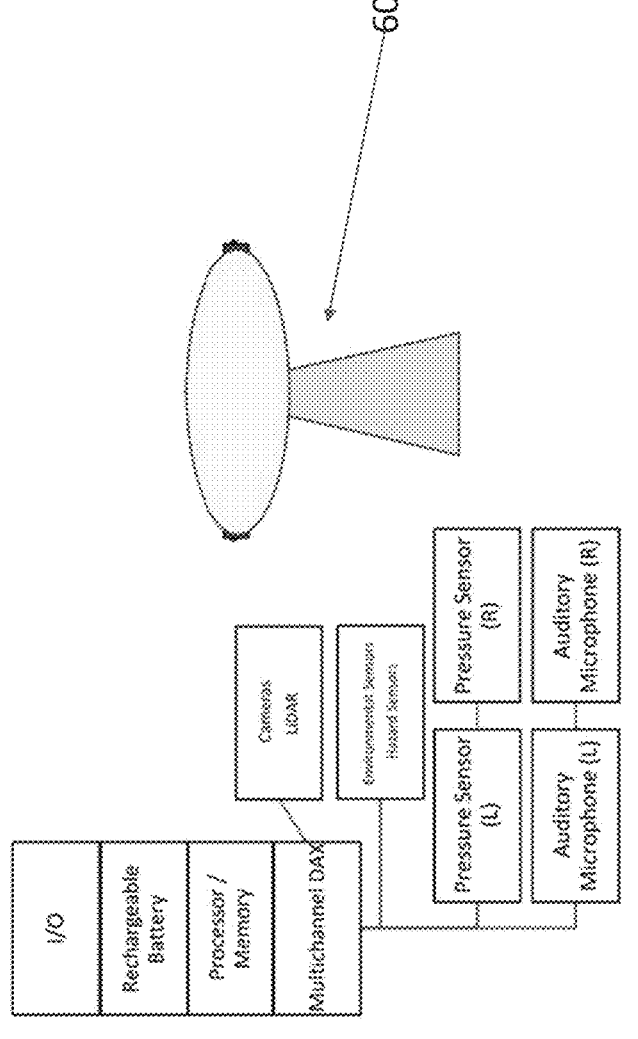
FIG. 13 shows the smart blast station embodiment of the present invention.
Figure 14:
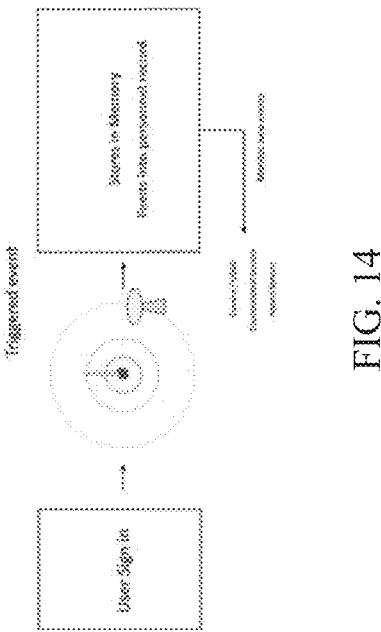
FIG. 14 shows a flow diagram of how user interacts with the smart blast station and a triggered event is fed into a user's personnel or medical record.

SENTINEL incorporates head-mounted system's configuration into blast station 60, as further shown at FIGS. 13 & 14. Preferably, blast station 60 is portable and mountable to surfaces. More preferably, blast station 60 operates in stand-alone mode to function as an environmental blast sensor system or integrated with user login and exposure monitoring by-proxy. Single or multiple users have the capability to sign into the station through the application to activate and use onboard unsupervised device-authenticated dosimetry. The shape of the parabolic disc shape of the main housing to the blast station was designed to facilitate on-plane incident and off-plane reflective pressure measurements of the blast overpressure for analytics and diagnostics of the event. FIG. 14 further shows how users interact with blast station 60 and describes how a triggered event is fed into a user's personnel or medical record.

This system also incorporates mitigation training aides that train users to be aware of their head position and high overpressure zones when operating weapon systems that may generate blast exposures. Preferably, a blast stand, which is a mitigation training aide, is designed to reduce harmful reflective blast exposure from the ground by elevating the user's shooting position. When coupled with a lower attenuating blast filter, reflective blast exposure may be further reduced. In another aspect of the preferred embodiment, an integrated blast station can be positioned indoors or outdoors to perform environmental monitoring and/or by-proxy user monitoring. The system can also interact with the Application to provide additional information and valuable data for the user.

Figure 15:
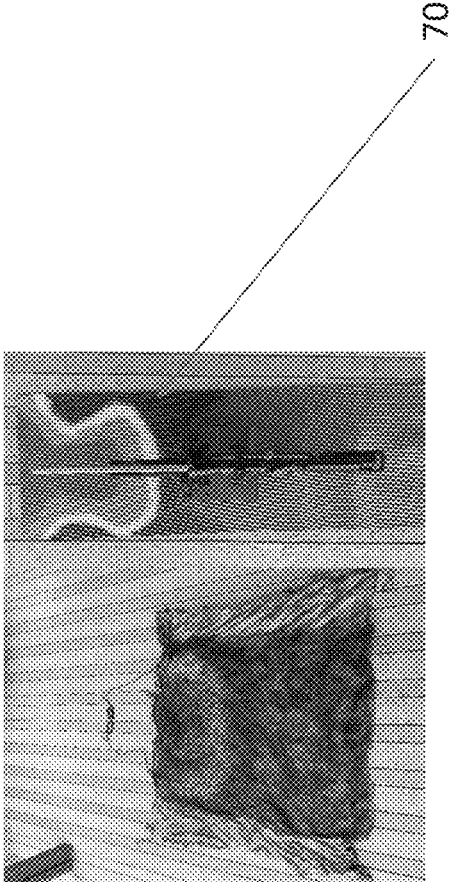
FIG. 15 shows one example of a blast mat contour pressure training aide. In this example the left side represents indirect fire systems. The right side is used for rifles.

The current state of the art lacks visualization training aides to demonstrate blast overpressure dissipation contours. As shown at FIG. 15, blast mat 70 is a portable training aide that overlays pressure contour maps from weapons that may generate a blast exposure. The contours represent pressure, either acoustic or overpressure, that dissipates from the location of the blast source, which can be either the back/venturi, breech, and/or muzzle. The material of blast mat 70 can be camo netting, foam, cotton, synthetic material, Kevlar, or any other similar or related material suited for this use. This system is scalable to weapon systems of all sizes and can be used as a training tool to understand pressure dissipation contours and potential exposure risk.

Optionally, the present invention provides for a scalable blast mat embodiment. It can be used as an educational tool to demonstrate blast overpressure dissipation contours to reinforce training and/or operational scenario to further understand blast exposure risk with associated weapons. These can take the form of a mouse pad, screensaver, chart, Application graphic, poster, billboard, or any other visual training aide.

The current state of the art lacks blast mitigation platforms to reduce blast overpressure exposure. During training, the allowable number of rounds (ANOR) is highly regulated to minimize acoustic and blast overpressure exposure risk. Generally, the ANOR for specific weapon system decreases from the standing, kneeling, and the prone firing position. This is related to increased exposure risk from reflecting surfaces, such as the ground. When the expanding blast wave strikes the surface of the earth or other surface, it is reflected off the ground to form a second shock wave traveling behind the first. This reflected wave travels faster than the first, or incident, shock wave since it is traveling through air already moving at high speed due to the passage of the incident wave. The reflected blast wave merges with the incident shock wave to form a single wave, known as the Mach Stem. The overpressure at the front of the Mach wave is generally about twice as great as that at the direct blast wave front.

One strategy to mitigate exposure from the Mach Stem is to remove reflective surfaces or increase the distance between the weapon system to the reflective surface. The blast stand of the present invention accomplishes this by elevating the operator and weapon system, thus increasing the distance between the weapon and the ground. Another strategy to minimize exposure risk is to attenuate the blast wave. Sound attenuating materials, either natural or synthetic materials, can be assembled in fashion to attenuate and vent pressure from the user's position.

Figure 16:
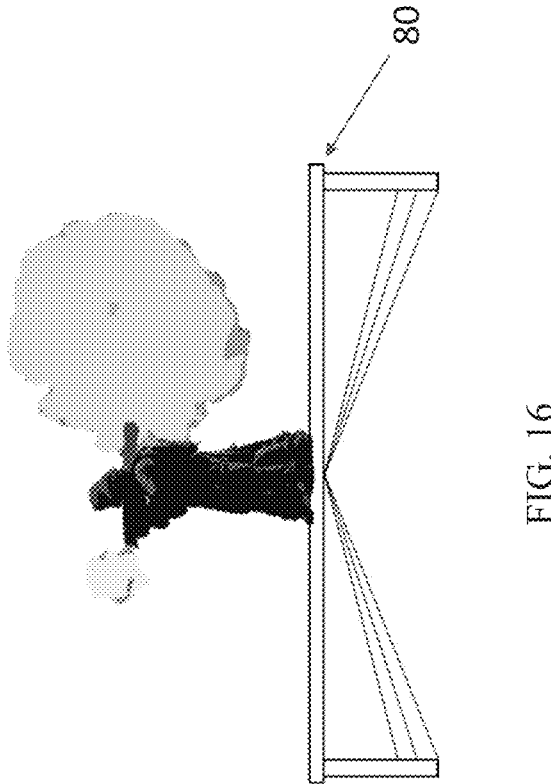
FIG. 16 shows an example of a blast stand with integrated blast filter. The size and height of the stand is scalable to the weapon systems of all sizes to increase the distance between the weapon system and known reflective surfaces to reduce the risks of reflective pressure exposure.

In a preferred embodiment of the present invention, the blast stand is a stationary firing platform to elevate the user off the ground during heavy weapon and rifle training (FIG. 16). Blast stand 80 has a changeable blast filter that attenuates primary and reflective overpressure from the user's location. The dimensions of the stand and filter are scalable to the weapon and its environment. Blast stand 80 increases the distance between the weapon system and a reflective surface. Preferably, blast stand 80 can be equipped with at least one material that reduces exposure levels from the reflective surface to the user. Optionally, the reflective surface is a firm area comprising at least one of a ground, wall, ceiling, structure or floor. Most preferably, blast stand 80 is positioned between the user and the reflective surface.

Preferably, the blast stand of the present invention is a multipurpose platform designed to decrease acoustic and blast overpressure exposure by increasing the distance between the weapon surface and the ground. Optionally, the blast stand also incorporates a blast attenuating filter to decrease and vent pressure away from the user's position to decrease the risk of reflective exposures.

EXAMPLES

Experiment 1: Risk-Based Model

Purpose: To illustrate the utility of risk-based monitoring, a simple study that assigns blast monitoring technologies to a user based upon the user's exposure profile can illustrate the utility of risk-based monitoring. The user is asked a series of questions to determine their exposure profile to different weapons, explosive devices, and frequency of use.

A user profile is then constructed from a user-derived database on use history (i.e., type of weapon, type of explosive device, and frequency of use). Weapon and explosive device pressure profile libraries are then queried to extrapolate a user exposure profile. The user exposure profile can be a series of discrete or continuous values, and can be converted into discrete categories (e.g., low, moderate, high). Users are then assigned corresponding technologies to match their exposure profile. The utility of this method can be easily tested by directly comparing exposure data (i.e., hits, misses, false positives, false negatives, peak overpressure, impulse, number of recorded peaks per hit, positive phase duration, etc.) from assigned technologies compared to traditional one size fits all blast monitoring devices and perform Receiver Operator Characteristic (ROC) analysis to determine whether the risk-based model is equivalent or superior to traditional blast exposure monitoring equipment.

Experiment 2: Supervised Dosimetry

Purpose: Demonstrate the capabilities of supervised dosimetry and its superiority to detect and confirm exposure to hazardous events over traditional dosimetry methods. The operational definition of a hit is any recording, either free-run or triggered, when user was exposed to a known hazard. The operational definition of a miss (false negative) is the lack of a recording, either free-run or triggered, when user was exposed to a known hazard. The operational definition of a false positive recording is any recording, either free-run or triggered, when the known hazard was absent.

Hits, misses, and false positive recordings from traditional dosimeters do not account for whether or not the dosimeter is actively being worn by the user, which can create inaccurate exposure histories. A simple method to reject false positive events can solve this problem. Therefore, the operational definition of a confirmed hit is any recording, either free-run or triggered, when a known hazard was present, and can be confirmed that the recording device was being worn by an outside observer. The operational definition of an unconfirmed hit is any recording, either free-run or triggered, when a known hazard was present, and cannot be confirmed that the recording device was being worn by an outside observer. The operational definition of a confirmed false positive is any recording, either free-run or triggered, when the known hazard was absent, and can be confirmed that the recording device was being worn by an outside observer. The operational definition of a unconfirmed false positive is any recording, either free-run or triggered, when the known hazard was absent, and cannot be confirmed that the recording device was being worn by an outside observer.

A simple experiment that identifies differences between "supervised" dosimetry compared to traditional dosimetry methods on the rate of positive exposure recordings and the incidence of false negative and false positive exposures recordings can be performed to demonstrate the superiority of supervised dosimetry over traditional dosimetry methods. The conditions to highlight these differences are: 1) device worn by user during known exposure to a hazard; 2) device exposed and user exposed to known hazard; 3) device exposed while the user is not exposed to known hazard; 4) device exposed in a vehicle while user is not present. The summary of this experiment is found at Table 1.

TABLE 1

| Summary of experimental differences between traditional and supervised dosimetry methods | | | | |
|---|---|---|---|---|
| | Condition 1 | Condition 2 | Condition 3 | Condition 4 |
| Traditional | Unconfirmed hit | Unconfirmed hit | Unconfirmed False Positive | Unconfirmed False Positive |
| Supervised | Confirmed hit | Confirmed hit | Confirmed False Positive | Confirmed False Positive |

Experiment 3: Head-Based Monitoring

A series of simple experiments can be performed to demonstrate the vectoring capabilities of the head-based monitoring system and the superiority of head-based monitoring to perform vectoring compared to traditional body worn systems.

The vectoring capability of the head-based monitoring system can be demonstrated by placing 2 wired blast gauge sensors on adjacent sides of the head or head-based accessory during controlled exposures around the system in 360 degrees of azimuth. If the distance between the blast gauge sensors is standardized at known distance, then arrival time and intensity differences can be easily used generate vector location maps of the known exposure. If the distance between the blast gauge sensors is at an unknown distance, then head-related transfer functions must be calculated and applied before arrival time and intensity differences can be used generate vector location maps of the known exposure.

Experiment 4: Mitigation Platform

The magnitude of the mitigation platform to decrease acoustic and overpressure exposure to users who operate weapons on the platform can be demonstrated by a series of experiments. The goal of the platform is to raise the location of the weapon system during operation off the ground to increase the distance of the weapon from a known reflective surface. Simple comparisons in user overpressure and acoustic exposure while changing the location of operation (i.e., ground, platform at 0.5 m and 1.0 m) and in different firing positions (e.g., prone. Kneeling and standing). If the distance between a weapon and reflective surfaces inversely related with overpressure and acoustic exposure, then a platform that elevates the weapon systems and user should yield a decrease in exposure level as the distance from the ground to the platform top increases.

All of the features disclosed in this claim may be combined in any combination. Each feature disclosed in this claim may be replaced by an alternative feature serving the same, equivalent, or similar purpose. Thus, unless expressly stated otherwise, each feature disclosed is only an example of a generic series of equivalent or similar features. As used in this claim and in the appended claims, the singular forms include the plural forms. For example, the terms "a," "an," and "the" include plural references unless the content clearly dictates otherwise. Additionally, the term "at least" preceding a series of elements is to be understood as referring to every element in the series. The inventions illustratively described herein can suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the future shown and described or any portion thereof, and it is recognized that various modifications are possible within the scope of the invention claimed. Thus, it should be understood that although the present invention has been specifically disclosed by preferred embodiments and optional features, modification and variation of the inventions herein disclosed can be resorted by those skilled in the art, and that such modifications and variations are considered to be within the scope of the inventions disclosed herein. The inventions have been described broadly and generically herein. Each of the narrower species and subgeneric groupings falling within the scope of the generic disclosure also form part of these inventions. This includes the generic description of each invention with a proviso or negative limitation removing any subject matter from the genus, regardless of whether or not the excised materials specifically resided therein. In addition, where features or aspects of an invention are described in terms of the Markush group, those schooled in the art will recognize that the invention is also thereby described in terms of any individual member or subgroup of members of the Markush group. It is also to be understood that the above description is intended to be illustrative and not restrictive. Many embodiments will be apparent to those of in the art upon reviewing the above description. The scope of the invention should, therefore, be determined not with reference to the above description, but should instead be determined with reference to the appended claims, along with the full scope of equivalents to which such claims are entitled. Those skilled in the art will recognize, or will be able to ascertain using no more than routine experimentation, many equivalents to the specific embodiments of the invention described. Such equivalents are intended to be encompassed by the following claims.

The invention claimed is:

1. A wearable system for simultaneously monitoring 360-degrees and mitigating exposure to occupational and environmental hazards to a user from weapons or devices, comprising:

(a) a body wearable system for the user to wear;

(b) at least two juxtaposed sensors connected to the wearable system to detect, monitor and record exposure to the environmental hazards;

(c) providing post-event monitoring for detection of changes in behavioral, physiological, and cognitive markers of head trauma, body trauma and environmental hazard exposure;

(d) a real time authentication dosimetry circuit configured as a closed loop biometric module verifying device wear and user attribution during exposure, wherein the dosimetry circuit is supervised or unsupervised; and (e) an onboard computer data acquisition system configured to convert, process, store, analyze, retrieve, alert, and transmit changes in voltage over time from at least one sensor, wherein the onboard computer can trigger a configuration routine, wherein the system is integrated into personal protection equipment worn by the user, wherein authenticated exposure data is transmitted to a computer system configured to initiate postprocessing and post-event protocols.

2. The wearable system of claim 1, wherein the system is integrated into a housing of a hearing protection element.

3. The wearable system of claim 1, wherein the system is attached to a housing of an ear protection element.

4. The wearable system of claim 1, wherein the sensors are configured to detect at least one occupational and environmental hazard selected from the group consisting of blast overpressure, acoustics, toxicants, chemicals, radiation, magnetic fields, electromagnetic energy, radio frequencies, coherent light sources and microwaves or a combination thereof.

5. The wearable system of claim 1, wherein the closed loop biometric module is further comprised of a microcontroller configured to compare sensor measured data to a stored standardized range for a user profile.

6. The wearable system of claim 1, wherein the onboard computer data acquisition system may be further comprised of: a digital signal processor; a solid-state memory module; firmware for implementing algorithms; a machine learning inference core; an inertial sensor; a microphone; and a power management system.

7. The wearable system of claim 1, wherein the plurality of sensors comprises unimodal or multimodal sensors further connected to at least one selected from the group consisting of a computer, microprocessor, controller unit, clock and memory, comprising:

(a) providing a head-mounted system for the user to wear; and (b) providing a means to calculate a vector of the exposure in relation to the user's head direction.

8. The wearable system of claim 5, wherein the closed-loop biometric module further comprises a microcontroller configured to compare measured bioelectric or physiological sensor data to a stored standardized range associated with a verified user profile in order to authenticate the wearer.

9. The wearable system of claim 5, wherein the microcontroller executes firmware that identifies sensor data when the measured values fall outside of the stored standardized range for longer than a predefined continuity interval for further analysis in order to prevent false exposure attribution.

10. The wearable system of claim 5, wherein the closed-loop biometric module further comprises a secure memory element configured to encrypt and store user profile parameters and comparison results prior to transmission to any external device.

11. The wearable system of claim 10, wherein the secure memory element employs a hardware-rooted routine that prevents modification or access to the stored user profile data without authentication of the device.

* * * * *